United States Patent [19]

Chan et al.

[11] Patent Number: 5,756,799
[45] Date of Patent: May 26, 1998

[54] CHIRAL PHOSPHINITES

[75] Inventors: Albert Sun-Chi Chan, Kowloon, Hong Kong; Yao-Zhong Jiang, Chengdu, China; Ai-Qiao Mi, Chengdu, China; Ming Yan, Chengdu, China; Wen-Hao Hu, Chengdu, China

[73] Assignee: The Hong Kong Polytechnic University, Kowloon, Hong Kong

[21] Appl. No.: 804,877

[22] Filed: Feb. 24, 1997

[51] Int. Cl.$^6$ .................................................. C07F 9/28
[52] U.S. Cl. ............................................ 558/156; 556/136
[58] Field of Search ......................... 558/156; 556/136

[56] References Cited

PUBLICATIONS

CA:112:985158 abs of "Asymmetric hydrogenation of alpha arylpropenoic acids catalyzed by rhodium I complexes of chiral ligands derived from soome monosaccharides", Sunjic, Gazz Chim Ital, 119(4) pp. 229–233, 1989.

CA:97:92397 abs of "Synthesis, conformational studies and enantioselective homogeneous catalytic hydrogenation with CRC–PHOS and some congeners", Comisso, Croat Chem Acta, 54(3), pp. 375–397, 1981.

Grubbs, Robert H. and Robert A. DeVries. "Asymmetric Hydro–Genation by an Atropisomeric Diphosphinite Rhodium Complex." *Tetrahedron Letters* No. 22 (1977) Pergamon Press. pp. 1879–1880.

Bakos, József, et al. "Use of Heterogeneous Asymmetric Hydro–genation for the Preparation of a Chiral Phosphinite and Its Application as a Ligand in Homogeneous Asymmetric Hydrogenation" *J. Org. Chem.* 46 (1981), 5427–5428.

Bakos, József, et al. "Asymmetric Hydrogenation Using Chiral Phosphinite Rhodium Complexes." *Tetrahedron Letters* vol. 25, No. 43 (1984) Pergamon Press. pp. 4965–4966.

Selke, R. and H. Pracejus. "Phosphinites of Carbohydrates as Chiral Ligands for Asymmetric Synthesis Catalysed by Complexes Part II: Superiority of Phenyl 4,6–O–(R)–Benzylidene–2,3–O–Bis(Diphenylphosphino)–β–D– Glucopyranoside for Rhodium(I)—Catalysed Hydrogenation of Amino Acid Precursors." *Journal of Molecular Catalysis* 37 (1986) 213–225.

Nieman, James A., et al. "An Improved Synthesis and Resolution of (±)–cis,cis–Spiro[4.4]Nonane–1,6–Diol." *Tetrahedron Asymmetry* vol. 4, No. 9(1993) Pergamon Press 1973–1976.

*Primary Examiner*—Gary Geist
*Assistant Examiner*—Jean F. Vollano
*Attorney, Agent, or Firm*—Leydig, Voit & Mayer, Ltd.

[57] ABSTRACT

New optically active phosphinite compounds which are useful in asymmetric catalysis have been synthesized and have been used in the preparation of rhodium catalysts. Such catalysts are particularly useful in enantioselective catalytic hydrogenation reactions.

26 Claims, No Drawings

CHIRAL PHOSPHINITES

FIELD OF INVENTION

This invention relates to a new class of organic compounds which are useful as auxiliaries in asymmetric synthesis for the production of a variety of chiral organic compounds.

BACKGROUND

In the asymmetric hydrogenation of prochiral compounds, excellent enantioselectivities were obtained by using suitable metal complexes of chiral diphosphines as catalysts. However, the preparation of diphosphine ligands sometimes are difficult while the corresponding diphosphinites are easier to prepare. Many diphosphinites with $C_2$-symmetry were investigated in the past twenty years. For example, BINAPO (Tetrahedron Letters, 1977, 22), BDPOP (J. Org.chem., 1981, 46(26), 5427), etc. were used as chiral ligands in the asymmetric catalytic hydrogenation of dehydroamino acid derivatives. However, the enantiomeric excess (e.e.) values of the products are generally much lower than those from the catalyst systems with chiral phosphine ligands. The replacement of the terminal $CH_3$ groups of BDPOP with phenyl groups gave a more enantioselective ligand BDPODP (Tetrahedron Letters, 1984, 25, 4965). However, the enantioselectivities of Rh(BDPODP) in the hydrogenation of methyl esters of enamides were only moderate. One example of diphosphinite (Ph-β- Glup, J. Molecular Catalysis, 1986, 37(2), 213–215) has been reported to be reasonably effective, which in the hydrogenation of dehydroamino acids led to high enantioselectivities (>90% e.e.). Unfortunately, only D-configuration of the ligands was readily available from the natural starting materials; the opposite configuration was not easily obtained.

SUMMARY OF THE INVENTION

This invention relates to a new class of novel organic compounds, namely (1S,5S,6S)- and (1R,5R,6R)-1,6-bis(diarylphosphinoxy)spiro[4.4]nonane (S-1 and R-1) and (1S,5S, 6S)- and (1R,5R,6R)-1,6-bis(dialkylphosphinoxy)spiro[4.4]nonane (S-2 and R-2).

This invention relates to the preparation of S-1, R-1, S-2, and R-2 in which (1S,5S,6S) or (1R,5R,6R)-spiro[4.4]nonane-1,6-diol (S-3 or R-3) is reacted with chlorodiarylphosphine or chlorodialkylphosphine in the presence of an organic base such as 4-N,N-dimethylaminopyridine and/or triethylamine.

This invention relates to the rhodium complexes containing 1 or 2 as effective catalysts for the asymmetric hydrogenation of prochiral substrates such as olefins to produce higher valued chiral products This invention also relates to the asymmetric catalytic hydrogenations of α,β-dehydroamino acid derivatives under mild conditions using the Rh-(1) or Rh-(2) as a catalyst. Chemical yields as high as 100% and optical yields as high as 100% can be obtained.

DETAILED DESCRIPTION

Herein, we designed and synthesized a class of novel phosphinite ligand containing a spirocylic backbone. The rhodium complexes of this new class of phosphinite were used as catalysts in the hydrogenation of dehydroamino acid derivatives. Quantitative chemical yields and up to 100% e.e. were obtained under very mild hydrogenation conditions (as low as one atmosphere of hydrogen pressure at room temperature in 10–60 minutes). The preparation of the rhodium catalyst is convenient. All of these advantages make the new phosphinites attractive for industrial application. Finally, both configurations of amino acids can be produced by using the respective rhodium complexes containing the S or R form of the novel ligand as catalyst.

The subject invention encompasses the hydrogenation reactions in which the catalyst thereof is a rhodium complex containing the said chiral phosphinite ligand.

The subject invention also relates to the spirocyclic diphosphinite ligand 1 and the synthetic route of the ligand.

The novel optically active ligands of this invention have the following structures

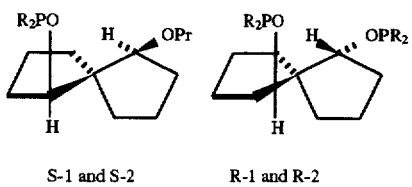

S-1 and S-2      R-1 and R-2 wherein:

(a) for ligands S-1 and R-1, R is chosen from the following groups:

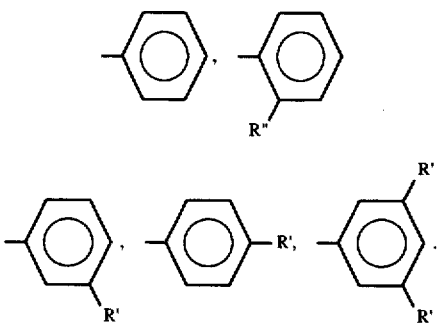

in which R' is a straight or branched chain alkyl group having from 1 to 6 carbon atoms, and R" is a straight or branched chain alkyl group having from 1 to 6 carbon atoms or an alkoxy group having from 1 to 6 carbon atoms; and (b) for ligands S-2 and R-2, R is a cycloalkyl group having from 4 to 8 carbon atoms.

The chiral ligand S-1, S-2 or R-1, R-2 can be easily prepared by the reaction of a suitable chlorophosphine with S-3 or R-3 in the presence of an organic base such as triethylamine.

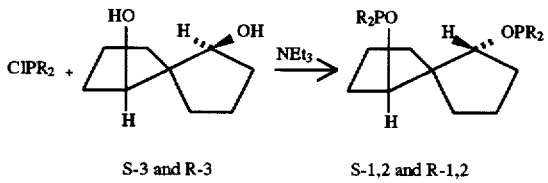

S-3 and R-3      S-1,2 and R-1,2

The preparation of S-3 and R-3 has been previously reported by Nieman et al. (Tetrahedron: Asymmetry, 1993, 1973)

For the purposes of this invention, the catalysts can be prepared in situ by the reaction of the pure optical isomer of 1 or 2 with $[Rh(COD)Cl]_2$ (where COD represent a cyclooctadiene group) in a suitable organic solvent such as tetrahydrofuran (THF), acetone, benzene, etc. to produce the rhodium complex containing 1 or 2. The chloride anion can be replaced with bromide or iodide ion. Alternatively, AgBF$_4$ can be added to the solution of Rh(COD)(1)Cl or Rh(COD)(2)Cl to produce [Rh(COD)(1)]BF$_4$ or [Rh(COD)(2)]BF$_4$. The BF$_4^-$ ion can be replaced with other non-coordinating or weakly coordinating anions such as ClO$_4^-$, PF$_6^-$, etc.

For the purposes of this invention, the rhodium complexes containing 1 or 2 can be used as catalysts in the hydrogenation of α,β-dehydroamino acid derivatives. Some illustrative examples of the precursors for the asymmetric hydrogenation are shown below.

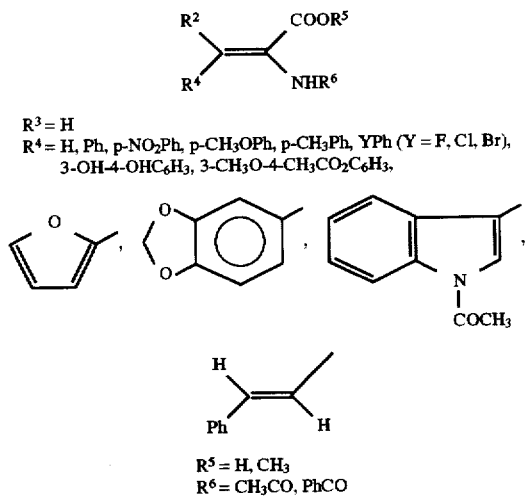

R$^3$ = H
R$^4$ = H, Ph, p-NO$_2$Ph, p-CH$_3$OPh, p-CH$_3$Ph, YPh (Y = F, Cl, Br), 3-OH-4-OHC$_6$H$_3$, 3-CH$_3$O-4-CH$_3$CO$_2$C$_6$H$_3$,

R$^5$ = H, CH$_3$
R$^6$ = CH$_3$CO, PhCO

The following examples of experiments are provided to illustrate but not to limit the scope of the usefulness of this invention. In said examples, the following abbreviations are used: THF=tetrahydrofuran, COD=cyclooctadiene, e.e.= enantiomeric excess.

EXAMPLE 1

Preparation of (1S,5S,6S)-1,6-Bis (diphenylphosphinoxy)spiro[4.4]nonane (S-1a)

(1S,5S,6S)-spiro[4.4]nonane-1,6-diol [S-3] prepared according to Nieman et al, *Tetrahedron: Asymmetry*, 1993, 1973–1975. (78 mg, 0.5 mmol), 4-N,N-dimethylaminopyridine (12.4 mg, 0.1 mmol) and triethylamine(101.9 mg, 1 mmol) in THF (3 ml) were charged to a 10 ml Schlenk flask under a dinitrogen atmosphere. This flask was cooled in an ice water bath. A solution of chlorodiphenylphosphine (0.18 ml, 1 mmol) in THF (1 ml) was added dropwise to the above solution with magnetic stirring. The ice water bath was removed and the mixture was stirred at room temperature for 8 hours. The solution was filtered to remove the solid triethylammonium chloride. The THF solvent was removed in vacuo to give 260 mg of S-1a. The product was good enough for the preparation of catalysts. For the purpose of obtaining crystalline material, the crude product was dissolved in approximately 10 ml anhydrous ethanol under heating. The saturated solution was cooled at 0° C. overnight. Filtration and drying under a stream of nitrogen gas gave 140 mg of white needle of S-1a (53.4% of theoretical yield). The analytical data for S-1a are as follows:

m.p.: 96°–96.5° C., [α]$_D$=+43.2 (c=0.104, CHCl$_3$), $^1$H-NMR (400 MHz, CDCl$_3$) δ: (1.33 m, 2H), 1.65–1.82 (m, 10H), 4.53 (d, J=5.3 Hz, 2H), 7.10–7.52 (m, 20H); $^{31}$P-NMR (160 MHz, CDCl$_3$): 102.8 ppm; $^{13}$C-NMR (100 MHz, CDCl$_3$) δ: 20.9, 32.5 (d, J$_{P-C}$=7.9 Hz), 33.1, 63.2, 87.3 (d, J$_{P-C}$=18.9 Hz), 128.5 (d, J$_{P-C}$=6.9 Hz), 128.7, 128.8 (d, J$_{P-C}$=8.8 Hz), 129.6, 130.0 (d, J$_{P-C}$=21.8 Hz), 130.9 (d, J$_{P-C}$=23.4 Hz), 143.4 (d, J$_{P-C}$12.0 Hz), 145.2 (d, J$_{P-C}$=21.8 Hz ); IR (KBr): 3060, 2968, 2907, 2868, 1486, 1440, 1348, 1104, 1006, 940, 742, 703 (cm$^{-1}$); Anal. Calcd for C$_{33}$H$_{34}$O$_2$P$_2$: C, 75.57; H, 6.48; P, 11.83. Found: C, 75.23; H, 6.41; P, 11.71.

EXAMPLE 2

Preparation of (1R,5R,6R)-1,6-Bis (diphenylphosphinoxy)spiro[4,4]nonane (R-1a)

The procedure was the same as in example 1 except that (−)-(1R, 5R,6R)-spiro[4,4]nonane-1,6-diol (R-3) prepared according to Nieman et al, *Tetrahedron: Asymmetry*, 1993, 1973–1975, instead of S-3 was used as starting material. The analytical data for R-1a are as follows:

m.p.: 96°–96.5° C., [α]$_D$=−43.2 (c=0.104, CHCl$_3$), $^1$H-NMR (400 MHz, CDCl$_3$) δ: (1.33 m, 2H), 1.65–1.82 (m, 10H), 4.53 (d, J=5.3 Hz, 2H), 7.10–7.52 (m, 20H); $^{31}$P-NMR (160 MHz, CDCl$_3$): 102.8 ppm; $^{13}$C-NMR (100 MHz, CDCl$_3$) δ: 20.9, 32.5 (d, J$_{P-C}$=7.9Hz), 33.1, 63.2, 87.3 (d, J$_{P-C}$=18.9 Hz), 128.5 (d, J$_{P-C}$=6.9 Hz), 128.7, 128.8 (d, J$_{P-C}$=8.8 Hz), 129.6, 130.0 (d, J$_{P-C}$=21.8 Hz), 130.9 (d, J$_{P-C}$=23.4 Hz), 143.4 (d, J$_{P-C}$=12.0 Hz), 145.2 (d, J$_{P-C}$=21.8 Hz); IR (KBr): 3060, 2968, 2907, 2868, 1486, 1440, 1348, 1104, 1006, 940, 742, 703 (cm$^{-1}$); Anal. Calcd for C$_{33}$H$_{34}$O$_2$P$_2$: C, 75.57; H, 6.48; P, 11.83. Found: C, 75.23; H, 6.41; P, 11.71.

EXAMPLE 3

Preparation of [Rh(COD)(S-1a)]BF$_4$ complex

[Rh(COD)Cl]$_2$ (purchased from Strem Chemicals, Inc., Newburyport, Mass.) (3.6 mg, 0.0073 mmol) and AgBF$_4$ (1.9 mg, 0.015 mmol) in THF (3 ml) were stirred at room temperature for 30 min. under a nitrogen atmosphere. The solution was filtered to remove the solid AgCl. After adding S-1a (7.8 mg, 0.015 mmol) (prepared according to Example 1) to the solution, [Rh(COD)(S-1a)]BF$_4$ was obtained in situ (0.005 mmol/ml). $^{31}$P-NMR (160 MHz, CD$_3$OD) δ: 125.1 ppm (d, J$_{Rh-P}$=177.1 Hz).

EXAMPLE 4

Preparation of [Rh(COD)(R-1a)]BF$_4$ complex

The THF solution of [Rh(COD)(R-1a)]BF$_4$ (0.005 mmol/ml) was prepared in situ with the same procedure as example 3 by using R-1a (prepared according to Example 2) instead of S-1a. $^{31}$P-NMR (160 MHz, CD$_3$OD) δ: 125.1 ppm (d, J$_{Rh-P}$=177.1 Hz).

EXAMPLE 5

Preparation of Rh(COD)(S-1a)Cl complex

Rh(COD)(S-1a)Cl was prepared in situ by stirring [Rh (COD)Cl]$_2$ (1.0 mg, 0.00202 mmol) and S-1a (2.33 mg, 0.00446 mmol) (prepared according to Example 1) in 0.5 ml benzene at room temperature for 30 min. under nitrogen atmosphere. $^{31}$P-NMR (160 MHz, CDCl$_3$) δ: 108.3 (d, J$_{Rh-P}$=168.7 Hz).

EXAMPLE 6

Preparation of Rh(COD)(R-1a) Cl complex

Benzene solution of Rh(COD)-(R-1a)Cl was prepared in situ through the same procedure as in example 5 by using R-1a (prepared according to Example 2) instead of S-1a.
$^{31}$P-NMR (160 MHz, CDCl$_3$) δ: 108.3 (d, J$_{Rh-P}$=168.7 Hz).

EXAMPLE 7

Asymmetric hydrogenation of methyl (Z)-2-acetamidocinnamate catalyzed by [Rh(COD)(S-1a)]BF$_4$ complex THF solution of [Rh(COD)(S-1a)]BF$_4$ (1 ml, 0.005 mmol) (prepared in example 3) and methyl (Z)-2-acetamidocinnamate (0.108g, 0.5 mmol) in methanol (20 ml) were charged to a 50 ml autoclave. The hydrogenation was carried out under 100 KPa of hydrogen pressure at room temperature for 10 min. A portion of the reaction mixture was analyzed by gas chromatography to determine the product composition. 100% conversion of the starting material to the hydrogenation product and 95.7% e.e. of methyl (S)-2-acetamido-3-phenylpropanoate were observed. Activated carbon (5 mg) was added to the solution and the mixture was stirred for 15 min. After filtration, the methanol solvent was evaporated to give a white solid of methyl (S)-2-acetamido-3-phenylpropanoate (0.106g), 95.7% e.e., yield 97.0%. (The enantiomeric excess was determined by chiral capillary GC using a Chrompack Chirasil-L-Val column.)

EXAMPLE 8

Asymmetric hydrogenation of methyl (Z)-2-acetamidocinnamate catalyzed by [Rh(COD)(R-1a)]BF$_4$ complex The hydrogenation was carried out through the same procedure as in example 7 using [Rh(COD)(R-1a)]BF$_4$ (prepared in example 4) instead of [Rh(COD)(S-1a)]BF$_4$ (prepared in example 3) to give the product methyl (R)-2-acetamido-3-phenylpropanoate, 95.6% e.e., 97.0% yield. (The enantiomeric excess was determined by the same method as in Example 7.)

EXAMPLE 9

Asymmetric hydrogenation of (Z)-2-acetamidocinnnamic acid catalyzed by [Rh(COD)(S-1a)]Cl complex A mixture of benzene solution of Rh(COD)(S-1a)Cl (0.5 ml, 0.0040 mmol) (prepared in example 5), (Z)-2-acetamidocinnamic acid (0.082 g, 0.404 nmol) and methanol (1.5 ml) was charged to a 50 ml autoclave. The hydrogenation was carried out under 100 KPa of hydrogen pressure at room temperature for 24 hours. Activated carbon was added and the solution was stirred for 15 min. After filtration, the solvent was evaporated to give a white product (S)-2-acetamido-3-phenylpropanoic acid in 96.2% yield and 81.2% e.e. (The enantiomeric excess was determined by the same method as in Example 7 after converting the products to methyl esters.)

EXAMPLE 10

Asymmetric hydrogenation of (Z)-2-acetamidocinnamic acid catalyzed by [Rh(COD)(R-1a)]Cl complex The hydrogenation proceeded through the same procedure as example 9 using Rh(COD)(R-1a)Cl (prepared in example 6) instead of Rh(COD)(S-1a)Cl (prepared in example 5) to give the product (R)-2-acetamido-3-phenylpropanoic acid in 96.2% yield and 81.6% e.e. (The enantiomeric excess was determined by the same method as in Example 9.)

EXAMPLE 11

Asymmetric hydrogenation of N-acetamidoacrylic acid catalyzed by [Rh(COD)(R-1a)]BF$_4$ complex A solution of [Rh(COD)(R-1a)]BF$_4$ (27 μl, 1.8×10$^{-4}$ mmol) (prepared in example 4) and 2-acetamidoacrylic acid (580 mg, 4.5 mmol) in 15 ml methanol was charged into a 50 ml autoclave under a nitrogen atmosphere. The autoclave was pressurized with 1350 KPa H$_2$ and the hydrogenation was carried out at room temperature for 1 hour. A portion of the reacting mixture was analyzed by gas chromatography to determine product composition. 100% conversion and 94.0% e.e. for the (R)-2-acetamido-propanoic acid product was obtained. The methanol was evaporated, ethylacetate (10 ml) and activated carbon (2 mg) were added and the mixture was refluxed for 10 min. After filtration, the hot ethyl acetate solution was allowed to cool to 0° C. White crystals were collected and washed with 5 ml of cold ethyl acetate to yield (R)-2-acetamidopropanoic acid (0.513 g) with 99.0% e.e. (87% isolated yield). mp 125° C., [α]$_D$=65.4 (c=1, H$_2$O). $^1$H-NMR (400MHz, D$_2$O) δ: 1.16 (d, 3H, J=7.2Hz), 1.77 (s, 3H), 4.07 (q, 1H, J=7.2Hz).

EXAMPLE 12

Other examples of hydrogenation of α,β-dehydroamino acid derivatives are shown below:

| Entry | R$_4$ | R$_5$ | R$_6$ | Cat*Rh | e.e. | Config. |
|---|---|---|---|---|---|---|
| 1 | Ph | CH$_3$ | CH$_3$ | [Rh(COD)(R-1a)]BF$_4$ | 95.6% | R |
| 2 | 4-CH$_3$—C$_6$H$_4$ | CH$_3$ | CH$_3$ | [Rh(COD)(R-1a)]BF$_4$ | 95.6% | R |
| 3 | 4-OCH$_3$—C$_6$H$_4$ | CH$_3$ | CH$_3$ | [Rh(COD)(R-1a)]BF$_4$ | 96.2% | R |
| 4 | 4-F—C$_6$H$_4$ | CH$_3$ | CH$_3$ | [Rh(COD)(R-1a)]BF$_4$ | 95.5% | R |
| 5 | 4-Cl—C$_6$H$_4$ | CH$_3$ | CH$_3$ | [Rh(COD)(R-1a)]BF$_4$ | 94.2% | R |
| 6 | 4-Br—C$_6$H$_4$ | CH$_3$ | CH$_3$ | [Rh(COD)(R-1a)]BF$_4$ | 96.3% | R |
| 7 | 4-NO$_2$—C$_6$H$_4$ | CH$_3$ | CH$_3$ | [Rh(COD)(R-1a)]BF$_4$ | 93.2% | R |
| 8 | 3,4-OCH$_2$O—C$_6$H$_4$ | CH$_3$ | CH$_3$ | [Rh(COD)(R-1a)]BF$_4$ | 94.9% | R |
| 9 | 2-Furfuryl | CH3 | CH$_3$ | [Rh(COD)(R-1a)]BF$_4$ | 97.2% | R |
| 10 | H | CH$_3$ | CH$_3$ | [Rh(COD)(R-1a)]BF$_4$ | 99.7% | R |

-continued

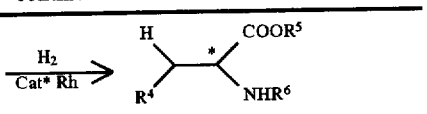

| Entry | R₄ | R₅ | R₆ | Cat*Rh | e.e. | Config. |
|---|---|---|---|---|---|---|
| 11 | 4-F—C₆H₄ | CH₃ | Ph | [Rh(COD)(R-1a)]BF₄ | 92.0% | R |
| 12 | 4-Cl—C₆H₄ | CH₃ | Ph | [Rh(COD)(R-1a)]BF₄ | 91.3% | R |
| 13 | 4-CH₃—C₆H₄ | CH₃ | Ph | [Rh(COD)(R-1a)]BF₄ | 93.7% | R |
| 14 | 2-Furfuryl | CH₃ | Ph | [Rh(COD)(R-1a)]BF₄ | 92.6% | R |
| 15 | Ph | H | CH₃ | [Rh(COD)(R-1a)]BF₄ | 97.9% | R |
| 16 | 2-Cl—C₆H₄ | H | CH₃ | [Rh(COD)(R-1a)]BF₄ | 97.3% | R |
| 17 | 3-Cl—C₆H₄ | H | CH₃ | [Rh(COD)(R-1a)]BF₄ | 97.4% | R |
| 18 | 4-Cl—C₆H₄ | H | CH₃ | [Rh(COD)(R-1a)]BF₄ | 97.3% | R |
| 19 | 4-NO₂—C₆H₄ | H | CH₃ | [Rh(COD)(R-1a)]BF₄ | 97.0% | R |
| 20 | H | H | CH₃ | [Rh(COD)(R-1a)]BF₄ | 100.0% | R |
| 21 | Ph | CH₃ | CH₃ | [Rh(COD)(S-1a)]BF₄ | 95.7% | S |
| 22 | 4-CH₃—C₆H₄ | CH₃ | CH₃ | [Rh(COD)(S-1a)]BF₄ | 96.6% | S |
| 23 | 4-OCH₃—C₆H₄ | CH₃ | CH₃ | [Rh(COD)(S-1a)]BF₄ | 96.6% | S |
| 24 | 4-F—C₆H₄ | CH₃ | CH₃ | [Rh(COD)(S-1a)]BF₄ | 91.4% | S |
| 25 | 4-Br—C₆H₄ | CH₃ | CH₃ | [Rh(COD)(S-1a)]BF₄ | 93.3% | S |
| 26 | 3,4-OCH₂O—C₆H₄ | CH₃ | CH₃ | [Rh(COD)(S-1a)]BF₄ | 94.0% | S |
| 27 | 2-Furfuryl | CH3 | CH₃ | [Rh(COD)(S-1a)]BF₄ | 96.8% | S |
| 28 | H | CH₃ | CH₃ | [Rh(COD)(S-1a)]BF₄ | 98.7% | S |
| 29 | C₆H₅CH=CH | CH₃ | CH₃ | [Rh(COD)(S-1a)]BF₄ | 59.2% | S |
| 30 | 3-(N-aceto)-indolyl | CH₃ | CH₃ | [Rh(COD)(S-1a)]BF₄ | 94.0% | S |
| 31 | 2-Furfuryl | CH₃ | Ph | [Rh(COD)(S-1a)]BF₄ | 92.6% | S |
| 32 | Ph | H | CH₃ | [Rh(COD)(R-1a)]Cl | 81.6% | R |
| 33 | 4-Cl—C₆H₄ | CH₃ | CH₃ | [Rh(COD)(R-1a)]Cl | 79.6% | R |
| 34 | 4-Cl—C₆H₄ | CH₃ | Ph | [Rh(COD)(R-1a)]Cl | 68.7% | R |
| 35 | Ph | H | CH₃ | [Rh(COD)(S-1a)]Cl | 81.2% | S |
| 36 | Ph | H | Ph | [Rh(COD)(S-1a)]Cl | 97.1% | S |
| 37 | Ph | CH₃ | Ph | [Rh(COD)(S-1a)]Cl | 74.9% | S |
| 38 | H | H | CH₃ | [Rh(COD)(S-1a)]Cl | 89.5% | S |

Reaction conditions: all the reactions were carried out at room temperature and under 100 KPa H₂ pressure within 10 min. to 24 hours to obtain 100% conversion, substrate/rhodium=100 (M/M).

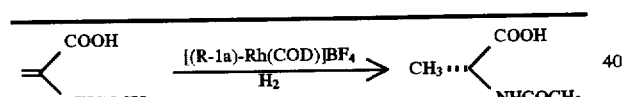

| Entry | Substrate/Catalyst (M/M) | P$_{H2}$ (KPa) | E.e. | Config. |
|---|---|---|---|---|
| 1 | 100 | 100 | 100.0% | R |
| 2 | 5000 | 1350 | 97.0% | R |
| 3 | 10000 | 1350 | 96.7% | R |
| 4 | 25000 | 1350 | 94.0% | R |

All the reactions were carried out at room temperature within 10–60 min to obtain 100% conversion. The catalyst used was [Rh(COD)(R-1a)]BF₄.

We claim:

1. An optically active spirocyclic phosphinite ligand S-1, S-2, R-1 having the following structure:

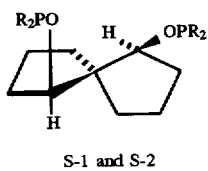

S-1 and S-2

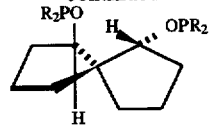

R-1 and R-2 wherein:
(a) for ligands S-1 and R-1, R is chosen from the following groups:

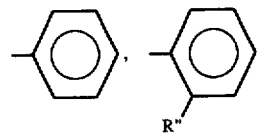

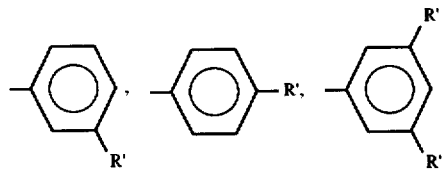

in which R' is a straight or branched chain alkyl group having from 1 to 6 carbon atoms, and R" is a straight or branched chain alkyl group having from 1 to 6 carbon atoms or an alkoxy group having from 1 to 6 carbon atoms; and (b) for ligands S-2 and R-2, R is a cycloalkyl group having from 4 to 8 carbon atoms.

2. An optically active spirocyclic phosphinite ligand according to claim 1 chosen from S-1 and R-1 wherein R is chosen from the following group:

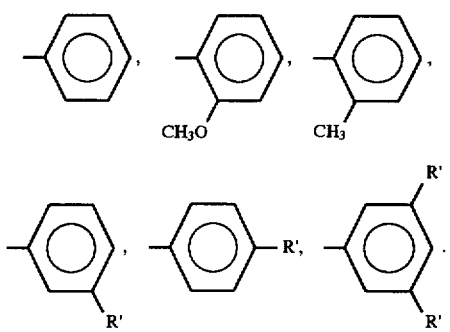

in which R' is chosen from the group consisting of methyl, ethyl, n-propyl, i-propyl and t-butyl groups.

3. An optically active spirocyclic phosphinite ligand according to claim 1 chosen from R-2 where R is chosen from cyclopentyl and cyclohexyl groups.

4. An optically active spirocyclic phosphinite ligand according to claim 1 chosen from (1S,5S,6S)- and (1R,5R,6R)-1,6-bis(diphenylphosphinoxy)spiro[4.4]nonane (S-1a and R-1a):

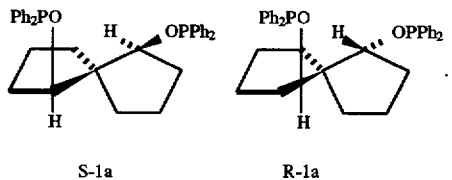

S-1a    R-1a

5. A chiral catalyst comprising a transition metal complex having an optically active ligand according to claim 1.

6. A chiral catalyst comprising a transition metal complex having an optically active ligand according to claim 4.

7. A chiral catalyst according to claim 6 chosen from the group consisting of Rh(COD)(S-1)X, Rh(COD)(R-1)X, Rh(COD)(S-2)X and RH(COD)(R-2)X, wherein COD is a cyclooctadiene group and X represents an anion chosen from the groups consisting of chloride, bromide, iodide, boron tetrafluoride, phosphorous hexachloride, perchlorate and tetraphenylboron anions.

8. A process for the hydrogenation of α,β-dehydroamino acid derivatives comprising reacting said derivatives with hydrogen in the presence of a catalyst according to claim 5.

9. A process for the hydrogenation of α,β-dehydroamino acid derivatives comprising reacting of said derivatives with hydrogen in the presence of a catalyst according to claim 6.

10. A process for the hydrogenation of α,β-dehydroamino acid derivatives comprising reacting of said derivatives with hydrogen in the presence of a catalyst according to claim 7.

11. A process according to claim 8 wherein the α,β-dehydroamino acid derivative is a compound having the following formula:

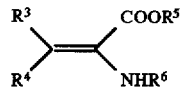

wherein:

$R^3$ represents a hydrogen atom;

$R^4$ is chosen from the group consisting of hydrogen atoms, phenyl groups, p-nitrophenyl groups, p-methoxyphenyl groups, p-methylphenyl groups, phenyl groups which are substituted by a halogen atom chosen from fluorine, chlorine and bromine atoms, 3,4-dihydroxyphenyl groups, 3-methoxy-4-methoxycarbonylphenyl groups, 2-furfuryl groups, 3-(N-acetyl)indolyl groups, styryl groups and 4-(1,2-methylenedioxy)phenyl groups;

$R^5$ is a hydrogen atom or a methyl group, and $R^6$ is an acetyl group or a benzoyl group.

12. A process according to claim 10 wherein the α,β-dehydroamino acid derivative is a compound having the following formula:

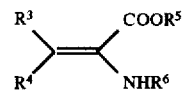

wherein:

$R^3$ represents a hydrogen atom;

$R^4$ is chosen from the group consisting of hydrogen atoms, phenyl groups, p-nitrophenyl groups, p-methoxyphenyl groups, p-methylphenyl groups, phenyl groups which are substituted by a halogen atom chosen from fluorine, chlorine and bromine atoms, 3,4-dihydroxyphenyl groups, 3-methoxy-4-methoxycarbonylphenyl groups, 2-furfuryl groups, 3-(N-acetyl)indolyl groups, styryl groups and 4-(1,2-methylenedioxy)phenyl groups;

$R^5$ is a hydrogen atom or a methyl group, and $R^6$ is an acetyl group or a benzoyl group.

13. A process according to claim 11 wherein the α,β-dehydroamino acid derivatives include 2-acetamidoacrylic acid.

14. A process according to claim 12 wherein the α,β-dehydroamino acid derivatives include 2-acetamidoacrylic acid.

15. A process according to claim 8 wherein the hydrogenation is performed at a hydrogen pressure of from 70 to 1350 Kpa, a reaction temperature range from −10° C. to 100° C. and at a molar ratio of substrate to catalyst of a range from 100 to 100,000.

16. A process according to claim 10 wherein the hydrogenation is performed at a hydrogen pressure of from 70 to 1350 Kpa, a reaction temperature range from −10° C. to 100° C. and at a molar ratio of substrate to catalyst of a range from 100 to 100,000.

17. A process according to claim 11 wherein the hydrogenation is performed at a hydrogen pressure of from 70 to 1350 Kpa, a reaction temperature range from −10° C. to 100° C. and at a molar ratio of substrate to catalyst of a range from 100 to 100,000.

18. A process according to claim 12 wherein the hydrogenation is performed at a hydrogen pressure of from 70 to 1350 Kpa, a reaction temperature of a range from −10° C. to 100° C. and at a molar ratio of substrate to catalyst of a range from 100 to 100,000.

19. A process according to claim 14 wherein the hydrogenation is performed at a hydrogen pressure of from 70 to 1350 Kpa, a reaction temperature of a range from −10° C. to 100° C. and at a molar ratio of substrate to catalyst of a range from 100 to 100,000.

20. A process according to claim 8 wherein the hydrogenation is performed at a hydrogen pressure of from 100 to 500 KPa, a reaction temperature of a range from −10° C. to 100° C. and at a molar ratio of substrate to catalyst of a range from 500 to 50,000.

21. A process according to claim 10 wherein the hydrogenation is performed at a hydrogen pressure of from 100 to 500 Kpa, a reaction temperature of a range from −10° C. to 100° C. and at a molar ratio of substrate to catalyst of a range from 500 to 50,000.

22. A process according to claim 11 wherein the hydrogenation is performed at a hydrogen pressure of from 100 to 500 Kpa, a reaction temperature of a range from −10° C. to 100° C. and at a molar ratio of substrate to catalyst of a range from 500 to 50,000.

23. A process according to claim 12 wherein the hydrogenation is performed at a hydrogen pressure of from 100 to 500 Kpa, a reaction temperature of a range from −10° C. to 100° C. and at a molar ratio of substrate to catalyst of a range from 500 to 50,000.

24. A process according to claim 14 wherein the hydrogenation is performed at a hydrogen pressure of from 100 to 500 Kpa, a reaction temperature of a range from −10° C. to 100° C. and at a molar ratio of substrate to catalyst of a range from 500 to 50,000.

25. A process according to claim 13 wherein the product is purified by recrystallisation using ethyl acetate as the recrystallisation solvent.

26. A process according to claim 14 wherein the product is purified by recrystallisation using ethyl acetate as the recrystallisation solvent.

* * * * *

UNITED STATES PATENT AND TRADEMARK OFFICE
CERTIFICATE OF CORRECTION

PATENT NO. : 5,756,799
DATED : May 26, 1998
INVENTOR(S) : CHAN et al.

It is certified that error appears in the above-identified patent and that said Letters Patent is hereby corrected as shown below:

TITLE PAGE

Item 30: Foreign Application Priority Data, Insert the following:

--October 24, 1996 [CH] China.............96117757.8--

Column 7, Line 58, after "R-1" insert --or R-2--;

Column 9, Line 48, after "reacting" delete --of--;

Line 51, after "reacting" delete --of--;

Signed and Sealed this

Sixteenth Day of March, 1999

Attest:

Q. TODD DICKINSON

*Attesting Officer*     *Acting Commissioner of Patents and Trademarks*